(12) United States Patent
Tormo i Blasco et al.

(10) Patent No.: US 7,335,661 B2
(45) Date of Patent: Feb. 26, 2008

(54) FUNGICIDAL MIXTURES

(75) Inventors: Jordi Tormo i Blasco, Laudenbach (DE); Thomas Grote, Wachenheim (DE); Eberhard Ammermann, Heppenheim (DE); Reinhard Stierl, Freinsheim (DE); Siegfried Strathmann, Limburgerhof (DE); Ulrich Schöfl, Brühl (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/532,770

(22) PCT Filed: Nov. 14, 2003

(86) PCT No.: PCT/EP03/12772

§ 371 (c)(1), (2), (4) Date: Apr. 27, 2005

(87) PCT Pub. No.: WO2004/045282

PCT Pub. Date: Jun. 3, 2004

(65) Prior Publication Data

US 2006/0074093 A1    Apr. 6, 2006

(30) Foreign Application Priority Data

Nov. 15, 2002    (DE) .................. 102 53 588

(51) Int. Cl.
*A01N 43/90* (2006.01)
*A01N 43/40* (2006.01)
(52) U.S. Cl. .................. 514/259.31; 514/355; 504/100
(58) Field of Classification Search ........... 514/259.31, 514/355; 504/100
See application file for complete search history.

(56) References Cited

U.S. PATENT DOCUMENTS

| | | | |
|---|---|---|---|
| 5,330,995 A | | 7/1994 | Eichen et al. |
| 5,589,493 A | * | 12/1996 | Eichen et al. ............... 514/355 |
| 5,593,996 A | | 1/1997 | Pees et al. |
| 6,262,091 B1 | | 7/2001 | Wagner et al. |
| 6,268,371 B1 | | 7/2001 | Sieverding et al. |
| 2007/0060579 A1 | * | 3/2007 | Wachendorff-Neumann et al. ............... 514/229.2 |

FOREIGN PATENT DOCUMENTS

| | | |
|---|---|---|
| AU | 199672129 B2 | 4/1997 |
| CA | 2 313 322 A1 | 7/1999 |
| CA | 2 434 695 A1 | 7/2002 |
| EP | 0 988 790 A | 3/2000 |
| JP | 02/56688 A | 7/2002 |
| WO | WO-97/10716 A | 3/1997 |
| WO | WO-98/46607 A | 10/1998 |
| WO | WO-99-31981 A | 7/1999 |
| WO | WO-02/56688 A | 7/2002 |

* cited by examiner

*Primary Examiner*—John Pak
(74) *Attorney, Agent, or Firm*—Birch, Stewart, Kolasch & Birch, LLP

(57) ABSTRACT

Fungicidal mixtures, comprising
A) the triazolopyrimidine of the formula I

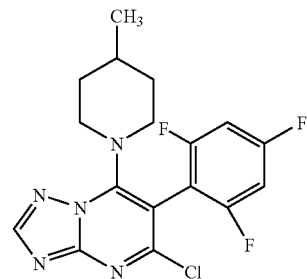

and
B) amide compounds of the formula II

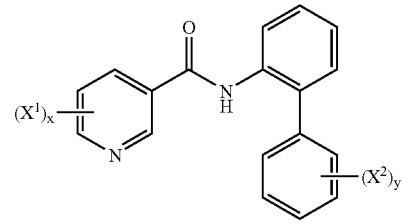

where $X^1$ and $X^2$ are halogen, nitro, cyano, alkyl, alkenyl, alkynyl, haloalkyl, haloalkenyl, haloalkynyl, alkoxy, haloalkoxy, haloalkylthio, alkylsulfinyl or alkylsulfonyl;
x is 1, 2, 3 or 4; and y is 1, 2, 3, 4 or 5;
in a synergistically effective amount, methods for controlling harmful fungi using mixtures of the compounds I and II, compositions comprising these compounds and the use of the compounds I and II for preparing such mixtures are described.

12 Claims, No Drawings

FUNGICIDAL MIXTURES

This application is a 371 of PCT/EP03/12772, filed on Nov. 14, 2003.

The present invention relates to fungicidal mixtures comprising
A) the triazolopyrimidine of the formula I

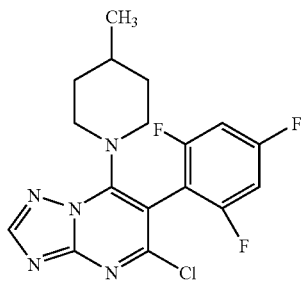

and
B) amide compounds of the formula II

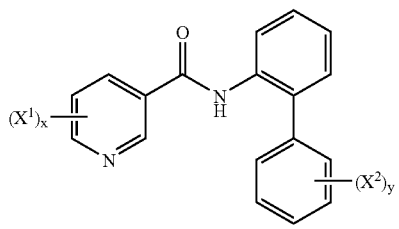

where $X^1$ and $X^2$ are identical or different and are halogen, nitro, cyano, $C_1$-$C_8$-alkyl, $C_2$-$C_8$-alkenyl, $C_2$-$C_8$-alkynyl, $C_1$-$C_8$-haloalkyl, $C_2$-$C_8$-haloalkenyl, $C_2$-$C_8$-haloalkynyl, $C_1$-$C_8$-alkoxy, $C_1$-$C_8$-haloalkoxy, $C_1$-$C_8$-haloalkylthio, $C_1$-$C_8$-alkylsulfinyl or $C_1$-$C_8$-alkylsulfonyl;

x is 1, 2, 3 or 4; and
y is 1, 2, 3, 4 or 5;

in a synergistically effective amount.

Moreover, the invention relates to methods for controlling harmful fungi using mixtures of the compounds I and II, to compositions comprising these mixtures and to the use of the compounds I and II for preparing such mixtures.

The compound of the formula I, 5-chloro-7-(4-methylpiperidin-1-yl)-6-(2,4,6-trifluorophenyl)-[1,2,4]triazolo[1,5-a]pyrimidine, its preparation and its action against harmful fungi are known from the literature (WO 98/46607).

Mixtures of triazolopyrimidines with other active compounds are generally known from EP-A 988 790 and U.S. Pat. No. 6,268,371.

Also known are the amide compounds of the formula II, their preparation and their action against harmful fungi (EP-A 545 099).

Mixtures of the amide compounds of the formula II with other active compounds are also known (WO 97/10716, WO 97/39628, WO 99/31981).

It is an object of the present invention to provide further particularly effective mixtures for controlling harmful fungi and in particular for certain indications. With a view to reducing the application rates and to improving the activity spectrum of the known compounds I and II, it was an object of the present invention to provide mixtures which, with reduced total amount of active compounds applied, have improved action against harmful fungi (synergistic mixtures).

We have found that this object is achieved by the mixtures defined at the outset. Moreover, it has been found that simultaneous, that is joint or separate, application of the compounds I and the compounds II or successive application of the compounds I and the compounds II allows better control of harmful fungi than is possible with the individual compounds alone.

The mixtures according to the invention have synergistic action and are therefore suitable for controlling harmful fungi and in particular powdery mildew fungi in cereals, vegetables, fruit, ornamental plants and grapevines.

The formula II represents in particular compounds in which $X^1$ is located in the 2-position and $X^2$ is located in the 4-position (formula II.1):

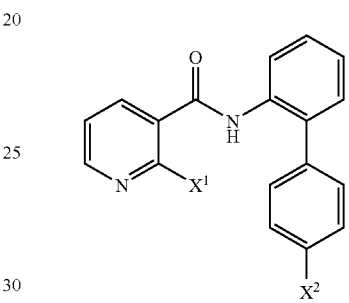

Preference is given to compounds of the formula II.1 in which the combination of the substituents corresponds to one row of Table 2 below:

| No. | $X^1$ | $X^2$ |
|---|---|---|
| II-1 | F | F |
| II-2 | F | Cl |
| II-3 | F | Br |
| II-4 | Cl | F |
| II-5 | Cl | Cl |
| II-6 | Cl | Br |
| II-7 | $CF_3$ | F |
| II-8 | $CF_3$ | Cl |
| II-9 | $CF_3$ | Br |
| II-10 | $CF_2H$ | F |
| II-11 | $CF_2H$ | Cl |
| II-12 | $CF_2H$ | Br |
| II-13 | $CH_3$ | F |
| II-14 | $CH_3$ | Cl |
| II-15 | $CH_3$ | Br |
| II-16 | $OCH_3$ | F |
| II-17 | $OCH_3$ | Cl |
| II-18 | $OCH_3$ | Br |
| II-19 | $SCH_3$ | F |
| II-20 | $SCH_3$ | Cl |
| II-21 | $SCH_3$ | Br |
| II-22 | $S(O)CH_3$ | F |
| II-23 | $S(O)CH_3$ | Cl |
| II-24 | $S(O)CH_3$ | Br |
| II-25 | $SO_2CH_3$ | F |
| II-26 | $SO_2CH_3$ | Cl |
| II-27 | $SO_2CH_3$ | Br |

Particular preference is given to compounds II.1 in which $X^1$ is $CF_3$ or halogen and $X^2$ is halogen, in particular to the compound II-5 (common name: boscalid).

When preparing the mixtures, it is preferred to employ the pure active compounds I and II, to which further compounds active against harmful fungi or other pests, such as insects, arachnids or nematodes, or else herbicidal or growth-regulating active ingredients or fertilizers can be added.

The mixtures of the compounds I and II, or the compounds I and II used simultaneously, together or separately, exhibit outstanding activity against a wide range of phytopathogenic fungi, in particular from the classes of the Ascomycetes, Deuteromycetes, Phycomycetes and Basidiomycetes. Some of them act systemically and can therefore also be employed as foliar- and soil-acting fungicides.

They are especially important for controlling a large number of fungi in a variety of crop plants, such as bananas, cotton, vegetable species (for example cucumbers, beans and cucurbits), barley, grass, oats, coffee, potatoes, corn, fruit species, rice, rye, soybean, tomatoes, grapevine, wheat, ornamentals, sugar cane, and a multiplicity of seeds.

They are particularly suitable for controlling the following phytopathogenic fungi: *Blumeria graminis* (powdery mildew) in cereals, *Erysiphe cichoracearum* and *Sphaerotheca fuliginea* in cucurbits, *Podosphaera leucotricha* in apples, *Uncinula necator* in grapevines, *Puccinia* species in cereals, *Rhizoctonia* species in cotton, rice and lawns, *Ustilago* species in cereals and sugar cane, *Venturia inaequalis* in apples, *Bipolaris* and *Drechslera* species in cereals, rice and lawns *Septoria nodorum* in wheat, *Botrytis cinera* in strawberries, vegetables, ornamentals and grapevines, *Mycosphaerella* species in bananas, groundnuts and cereals, *Pseudocercosporella herpotrichoides* in wheat and barley, *Pyricularia oryzae* in rice, *Phytophthora infestans* in potatoes and tomatoes, *Pseudoperonospora* species in cucurbits and hops, *Plasmopara viticola* in grapevines, *Alternaria* species in vegetables and fruit and also *Fusarium* and *Verticillium* species.

Moreover, they can be used in the proteection of materials (for example the protection of wood), for example against *Paecilomyces variotii*.

The compounds I and II can be applied simultaneously, that is together or separately, or in succession, and the sequence here, in the case of separate application, does not generally have any effect on the result of the control measures.

The compounds I and II are usually applied in a weight ratio of from 100:1 to 1:100, in particular from 20:1 to 1:20, preferably from 20:1 to 1:5.

Depending on the kind of effect desired, the application rates of the mixtures according to the invention are, in particular in agricultural crop areas, from 5 to 2000 g/ha, preferably from 50 to 1500 g/ha, in particular from 50 to 750 g/ha.

The application rates here of the compounds I are from 5 to 2000 g/ha, preferably from 50 to 1500 g/ha, in particular from 5 to 750 g/ha.

Correspondingly, in the case of the compounds II, the application rates are from 5 to 2000 g/ha, preferably from 50 to 1500 kg/ha, in particular from 50 to 750 kg/ha.

For seed treatment, the application rates of the mixture are generally from 0.001 to 1 g/kg of seed, preferably from 0.01 to 0.5 g/kg, in particular from 0.01 to 0.1 g/kg.

If phytopathogenic harmful fungi are to be controlled, the separate or joint application of the compounds I and II or of the mixtures of the compounds I and II is effected by spraying or dusting the seeds, the plants or the soils before or after sowing of the plants, or before or after plant emergence.

The mixtures according to the invention or the compounds I and II can be converted into the customary formulations, for example solutions, emulsions, suspensions, dusts, powders, pastes and granules. The application form depends on the particular purpose; in each case, it should ensure a fine and uniform distribution of the compound according to the invention.

The formulations are prepared in a known manner, for example by extending the active compound with solvents and/or carriers, if desired using emulsifiers and dispersants. Solvents/auxiliaries which are suitable are essentially:

water, aromatic solvents (for example Solvesso products, xylene), paraffins (for example mineral fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used.

carriers such as ground natural minerals (for example kaolins, clays, talc, chalk) and ground synthetic minerals (for example highly disperse silica, silicates); emulsifiers such as nonionic and anionic emulsifiers (for example polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compounds. The active compounds are employed in a purity of from 90% to 100%, preferably 95% to 100% (according to NMR spectrum).

The following are examples of formulations:

1. Products for Dilution with Water

A) Soluble Concentrates (SL)

10 parts by weight of the active compounds are dissolved in water or in a water-soluble solvent. As an alternative, wetters or other auxiliaries are added. The active compound dissolves upon dilution with water.

B) Dispersible Concentrates (DC)

20 parts by weight of the active compounds are dissolved in cyclohexanone with addition of a dispersant, for example polyvinylpyrrolidone. Dilution with water gives a dispersion.

C) Emulsifiable Concentrates (EC)

15 parts by weight of the active compounds are dissolved in xylene with addition of calcium dodecylbenzenesulfonate and castor oil ethoxylate (in each case 5% strength). Dilution with water gives an emulsion.

D) Emulsions (EW, EO)

40 parts by weight of the active compounds are dissolved in xylene with addition of calcium dodecylbenzenesulfonate and castor oil ethoxylate (in each case 5% strength). This mixture is introduced into water by means of an emulsifier (Ultraturax) and made into a homogeneous emulsion. Dilution with water gives an emulsion.

E) Suspensions (SC, OD)

In an agitated ball mill, 20 parts by weight of the active compounds are comminuted with addition of dispersants, wetters and water or an organic solvent to give a fine active compound suspension. Dilution with water gives a stable suspension of the active compound.

F) Water-dispersible Granules and Water-soluble Granules (WG, SG)

50 parts by weight of the active compounds are ground finely with addition of dispersants and wetters and made into water-dispersible or water-soluble granules by means of technical appliances (for example extrusion, spray tower, fluidized bed). Dilution with water gives a stable dispersion or solution of the active compound.

G) Water-dispersible Powders and Water-soluble Powders (WP, SP)

75 parts by weight of the active compounds are ground in a rotor-stator mill with addition of dispersants, wetters and silica gel. Dilution with water gives a stable dispersion or solution with the active compound.

2. Products to be Applied Undiluted

H) Dustable Powders (DP)

5 parts by weight of the active compounds are ground finely and mixed intimately with 95% of finely divided kaolin. This gives a dustable product.

I) Granules (GR, FG, GG, MG)

0.5 part by weight of the active compounds is ground finely and associated with 95.5% carriers. Current methods are extrusion, spray-drying or the fluidized bed. This gives granules to be applied undiluted.

J) ULV Solutions (UL)

10 parts by weight of the active compounds are dissolved in an organic solvent, for example xylene. This gives a product to be applied undiluted.

The active compounds can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; it is intended to ensure in each case the finest possible distribution of the active compounds according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1%.

The active compounds may also be used successfully in the ultra-low-volume process (ULV), it being possible to apply formulations comprising over 95% by weight of active compound, or even to apply the active compound without additives.

Various types of oils, wetters, adjuvants, herbicides, fungicides, other pesticides, or bactericides may be added to the active compounds, if appropriate just immediately prior to use (tank mix). These agents can be admixed with the agents according to the invention in a weight ratio of 1:10 to 10:1.

The compounds I and II or the mixtures or the corresponding formulations are applied by treating the harmful fungi or the plants, seeds, soils, areas, materials or spaces to be kept free from them with a fungicidally effective amount of the mixture or, in the case of separate application, of the compounds I and II. Application can be carried out before or after infection by the harmful fungi.

The fungicidal action of the compound and the mixtures can be demonstrated by the experiments below:

The active compounds, separately or jointly, were prepared as a stock solution with 0.25% by weight of active compound in acetone or DMSO. 1% by weight of the emulsifier Uniperol® EL (wetting agent having emulsifying and dispersing action based on ethoxylated alkylphenols) was added to this solution, and the solution was diluted with water to the desired concentration.

USE EXAMPLE 1

Curative Activity Against Wheat Leaf Rust Caused by *Puccinia recondita*

Leaves of potted wheat seedlings of the cultivar "Kanzler" were dusted with spores of leaf rust (*Puccinia recondita*). For 24 hours, the pots were then placed at 20-22_C in a chamber with high atmospheric humidity (90-95%). During this time, the spores germinated and the germinal tubes penetrated into the leaf tissue. The next day, the infected plants were sprayed to runoff point with an aqueous suspension having the concentration of active compounds stated below. The suspension or emulsion was prepared as described above. After the spray coating had dried on, the test plants were cultivated in a greenhouse at 20-22_C and 65-70% relative atmospheric humidity for 7 days. The extent of rust fungus development on the leaves was then determined.

Evaluation was carried out by determining the infected leaf areas as a percentage. These percentages were converted into efficacies. The efficacy (W) was calculated as follows using Abbot's formula:

$W = (1-a/b) \cdot 100$ a corresponds to the fungal infection of the treated plants in % and b corresponds to the fungal infection of the untreated (control) plants in %

An efficacy of 0 means that the infection level of the treated plants corresponds to that of the untreated control plants; an efficacy of 100 means that the treated plants were not infected.

The expected efficacies of the mixtures of the active compounds were determined using Colby's formula [R. S. Colby, Weeds 15, 20-22 (1967)] and compared with the observed efficacies.

Colby's formula: $E = x + y - x \cdot y/100$

E expected efficacy, expressed as % of the untreated control, when using the mixture of the active compounds A and B at the concentrations a and b x efficacy, expressed as % of the untreated control, when using active compound A at a concentration a y efficacy, expressed as % of the untreated control, when using active compound B at a concentration b

TABLE A

Individual active compounds

| Example | Active compound | Concentration of active compound in the spray liquor [ppm] | Efficacy in % of the untreated control |
|---|---|---|---|
| 1 | Control (untreated) | | (90% infection) |
| 2 | I | 4 | 56 |
|   |   | 1 | 0 |
| 3 | II-5 (boscalid) | 4 | 0 |
|   |   | 0.25 | 0 |

TABLE B

Mixtures according to the invention

| Example | Mixture of active compounds Concentration Mixing ratio | Observed efficacy | Calculated efficacy* |
|---|---|---|---|
| 4 | I + II-5<br>4 + 0.25 ppm<br>16:1 | 92 | 56 |
| 5 | I + II-5<br>4 + 4 ppm<br>1:1 | 92 | 56 |
| 6 | I + II-5<br>1 + 4 ppm<br>1:4 | 33 | 0 |

*)efficacy calculated using Colby's formula

USE EXAMPLE 2

Activity Against Gray Mold on Bellpepper Leaves Caused by *Botrytis cinerea*, Protective Application Bellpepper seedlings of the cultivar "Neusiedler Ideal Elite" were, after 4-5 leaves were well developed, sprayed to runoff point with an aqueous suspension having the active compound concentration stated below. The next day, the treated plants were inoculated with a spore suspension of *Botrytis cinerea* which contained $1.7 \times 10^6$ spores/ml in a 2% strength aqueous biomalt solution. The test plants were then placed in a climatized chamber at 22-24_C and high atmospheric humidity. After 5 days, the extent of the fungus development on the leaves could be determined visually in %.

Evaluation was carried out analogously to example 1.

TABLE C

Individual active compounds

| Example | Active compound | Concentration of active compound in the spray liquor [ppm] | Efficacy in % of the untreated control |
|---|---|---|---|
| 7 | Control (untreated) | | (95% infection) |
| 8 | I | 4 | 68 |
|   |   | 1 | 37 |
|   |   | 0.25 | 0 |
| 9 | II-5 (boscalid) | 1 | 0 |
|   |   | 0.25 | 0 |

TABLE D

Mixtures according to the invention

| Example | Mixture of active compounds Concentration Mixing ratio | Observed efficacy | Calculated efficacy* |
|---|---|---|---|
| 10 | I + II-5<br>4 + 0.25 ppm<br>16:1 | 95 | 68 |
| 11 | I + II-5<br>1 + 1 ppm<br>1:1 | 100 | 37 |
| 12 | I + II-5<br>0.25 + 0.25 ppm<br>1:1 | 79 | 0 |
| 13 | I + II-5<br>0.25 + 1 ppm<br>1:4 | 89 | 0 |

*)efficacy calculated using Colby's formula

The test results show that in all mixing ratios the efficacy observed for the combinations according to the invention is higher than that calculated beforehand using Colby's formula.

We claim:
1. A fungicidal mixture comprising:
A) the triazolopyrimidine of the formula I,

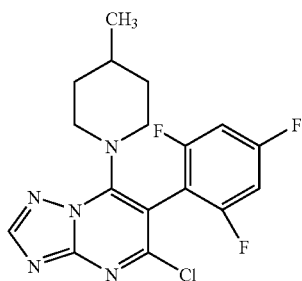

and
B) an amide compound which corresponds to formula II-1

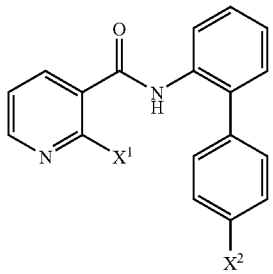

in which $X^1$ is $CF_3$ or halogen and $X^2$ is halogen, wherein the weight ratio of the triazolopyrimidine I to the amide compound of formula II-1 is from 20:1 to 1:20.

2. A fungicidal composition, comprising the fungicidal mixture as claimed in claim 1 and a solid or liquid carrier.

3. A fungicidal mixture as claimed in claim 1, wherein the weight ratio of the triazolopyrimidine I to the amide compound of formula II-1 is from 16:1 to 1:4.

4. A method for controlling phytopathogenic harmful fungi, which comprises treating the harmful fungi, their habitat or the plants, seeds, soils, areas, materials or spaces to be kept free from them with the fungicidial mixture of claim 1.

5. A method as claimed in claim 4, wherein the triazolopyrimidine of the formula I and the amide compound of the formula II-1 are applied simultaneously, that is either together or separately, or in succession to form the fungicidial mixture.

6. A method as claimed in claim 4, wherein the triazolopyrimidine of the formula I is applied in an amount of from 5 to 2000 g/ha.

7. A method as claimed in claim 4, wherein the amide compound of the formula II-1 is applied in an amount of from 5 to 2000 g/ha.

8. A fungicidal mixture comprising:
A) the triazolopyrimidine of the formula I,

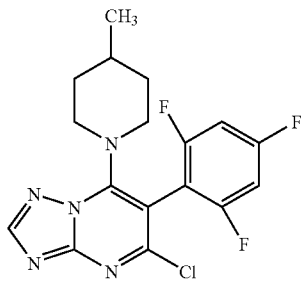

and
B an amide compound of formula II-5

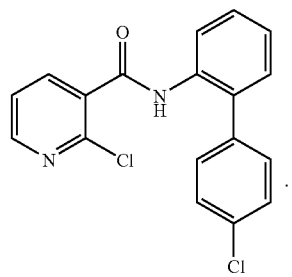

9. A fungicidal composition, comprising the fungicidal mixture as claimed in claim 8 and a solid or liquid carrier.

10. A fungicidal mixture as claimed in claim 8, wherein the weight ratio of the triazolopyrimidine I to the amide compound of formula II-5 is from 16:1 to 1:4.

11. A method for controlling phytopathogenic harmful fungi, which comprises treating the harmful fungi, their habitat or the plants, seeds, soils, areas, materials or spaces to be kept free from them with the fungicidal mixture of claim 8.

12. A method as claimed in claim 11, wherein the triazolopyrimidine of the formula I the and amide compound of the formula II-5 are applied simultaneously, that is either together or separately, or in succession to form the fungicidial mixture.

* * * * *